United States Patent [19]

Sprecker et al.

[11] Patent Number: 5,077,273
[45] Date of Patent: Dec. 31, 1991

[54] EPOXYOCTAHYDRODIME-THYLACETONAPHTHONES, AND PERFUMERY USES THEREOF

[75] Inventors: Mark A. Sprecker, Sea Bright; Robert P. Belko, Woodbridge; Kathleen E. Boardwick, Keyport, all of N.J.

[73] Assignee: International Flavors & Fragrances Inc., New York, N.Y.

[21] Appl. No.: 701,085

[22] Filed: May 16, 1991

[51] Int. Cl.$^5$ ................................................ A61K 7/46
[52] U.S. Cl. ........................................ 512/13; 549/545
[58] Field of Search .................... 512/13, 17; 549/545

[56] References Cited

U.S. PATENT DOCUMENTS

| | | | |
|---|---|---|---|
| 3,647,826 | 3/1972 | Hall | 549/545 |
| 3,907,321 | 9/1975 | Hall | 131/275 |
| 3,911,018 | 10/1975 | Hall et al. | 512/17 |
| 4,634,548 | 1/1987 | Helmhinger et al. | 512/13 |
| 4,933,319 | 6/1990 | Sprecker et al. | 549/545 |

Primary Examiner—James H. Reamer
Attorney, Agent, or Firm—Arthur L. Liberman

[57] ABSTRACT

Described are epoxyoctahydrodimethylacetonaphthones defined according to the generic structure:

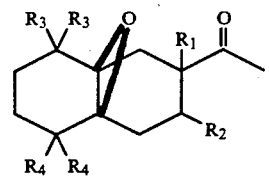

wherein $R_1$, $R_2$, $R_3$ and $R_4$ each represents methyl or hydrogen with the proviso that one of $R_3$ or $R_4$ is methyl and the other of $R_3$ or $R_4$ is hydrogen; and perfumery uses thereof in augmenting or enhancing the aroma of perfume compositions, colognes and perfumed articles, including solid or liquid anionic, cationic, nonionic or zwitterionic detergents, fabric softener compositions, fabric softener articles, cosmetic powders, hair preparations and perfumed polymers.

20 Claims, 8 Drawing Sheets

FIG.I
GLC PROFILE FOR EXAMPLE I.

EPOXYOCTAHYDRODIMETHYLACETONAPHTHONES, AND PERFUMERY USES THEREOF

BACKGROUND OF THE INVENTION

This invention relates to epoxyoctahydrodimethylacetonaphthones defined according to the generic structure:

wherein $R_1$, $R_2$, $R_3$ and $R_4$ each represents methyl or hydrogen with the proviso that one of $R_3$ or $R_4$ is methyl and the other of $R_3$ or $R_4$ is hydrogen and uses thereof in augmenting or enhancing the aroma of perfume compositions, colognes and perfumed articles.

There has been considerable work performed relating to substances which can be used impart, modify, augment or enhance aromas in perfumed articles, perfume compositions and colognes. These substances are used to diminish the use of natural materials, some of which may be in short supply and to provide more uniform properties in the finished product.

Patchouli, musky, sweet, woody, animalic and civet aromas with woody and patchouli topnotes are particularly desirable in augmenting or enhancing the aroma of perfume compositions, colognes and perfumed articles (e.g., solid or liquid anionic, cationic, nonionic or zwitterionic detergents, fabric softener compositions, fabric softener articles, hair preparations, cosmetic powders and perfumed polymers).

Perfumery uses of octahydrodimethylacetonaphthones are disclosed in the prior art, for example, in U.S. Pat. No. 3,907,321 issued on Sept. 23, 1975 where the compound having the structure:

is disclosed as a product capable of augmenting or enhancing the aroma of perfume compositions as well as tobaccos. One of the isomers is indicated to have a characteristic intense fruity, amber note.

However, no suggestion is indicated therein or in any other prior art that such compound can be epoxidized in order to produce the epoxyoctahydrodimethylacetonaphthones of the instant invention. Furthermore, there is no suggestion that such epoxyoctahydrodimethylacetonaphthones of the instant invention have the unobvious, unexpected and advantageous perfumery properties that the epoxyoctahydrodimethylacetonaphthones of our invention have.

BRIEF DESCRIPTION OF THE DRAWINGS

and

and prepared according to Example I.

FIG. 2A is a detailed drawing of the section indicated as "A" in the NMR spectrum of FIG. 2.

FIG. 2B is a detailed section of that part of the NMR spectrum of FIG. 2 indicated by "B".

prepared according to Example II.

FIG. 4A is the detailed section of the NMR spectrum of FIG. 4 indicated by "A".

DETAILED DESCRIPTION OF THE DRAWINGS

Figure 1:
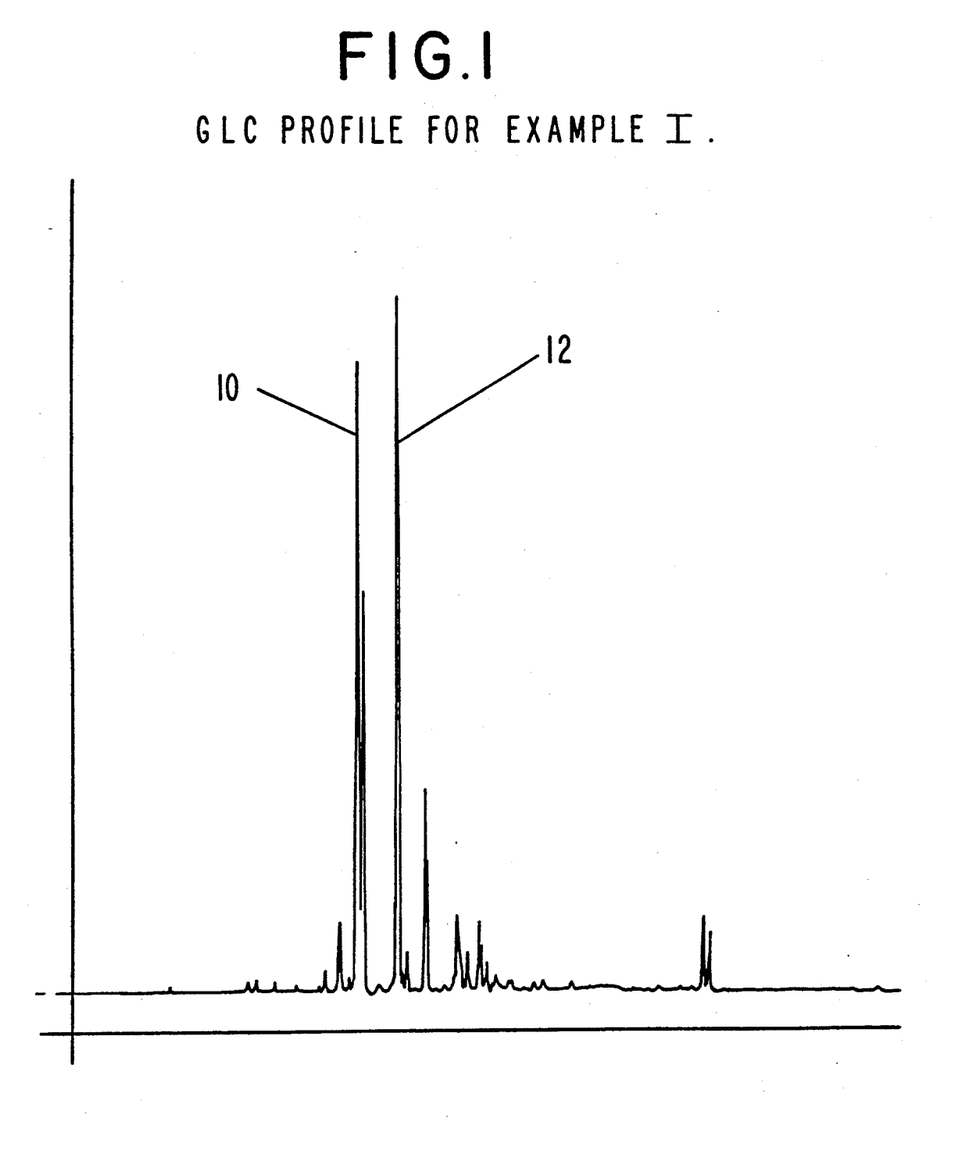
FIG. 1 is the GLC profile (capillary GLC) of the reaction product of Example I containing the compounds having the structures.
Figure 3:
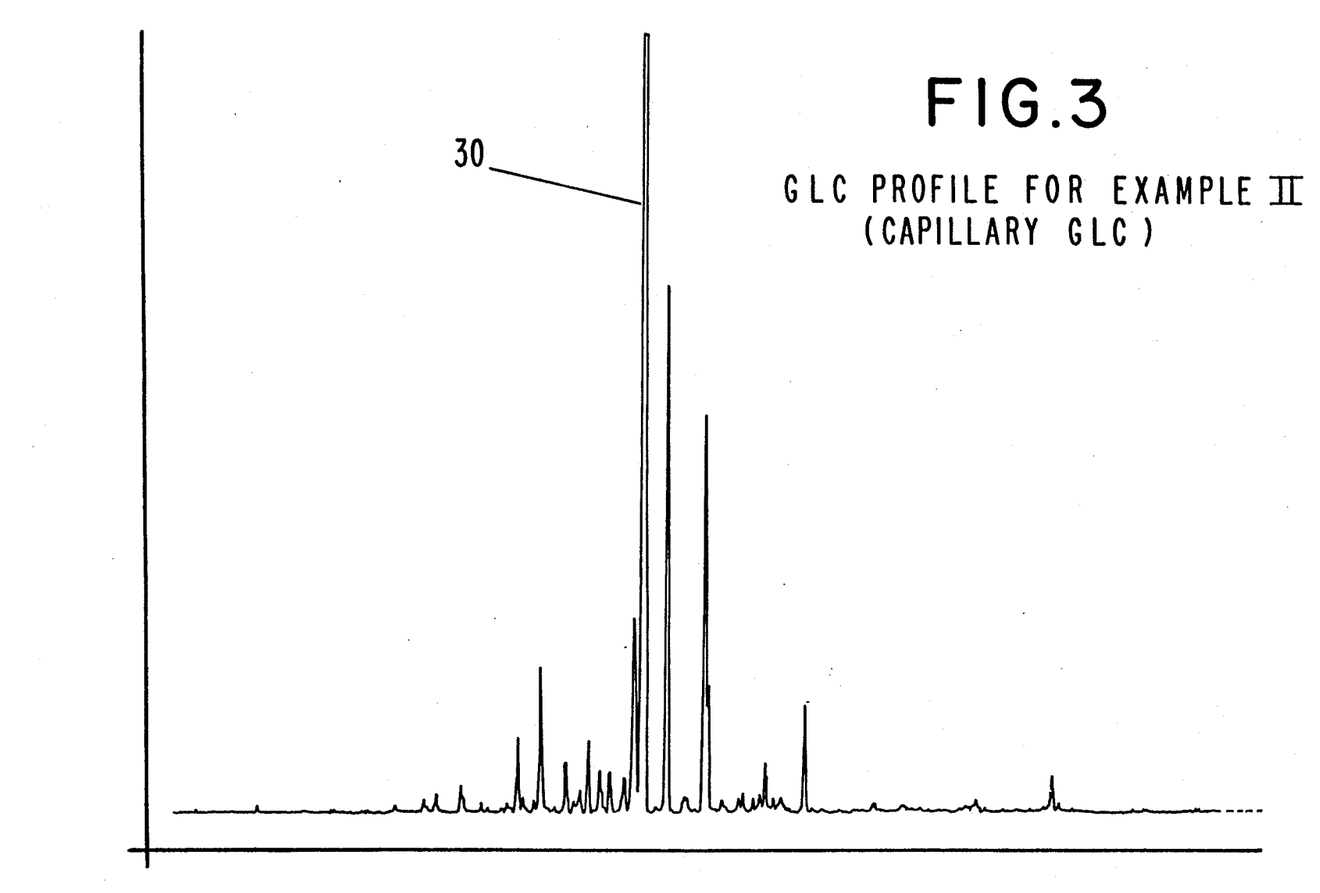
FIG. 3 is the GLC profile (capillary GLC) for the reaction product of Example II containing the compound having the structure.
Figures 5, 6:
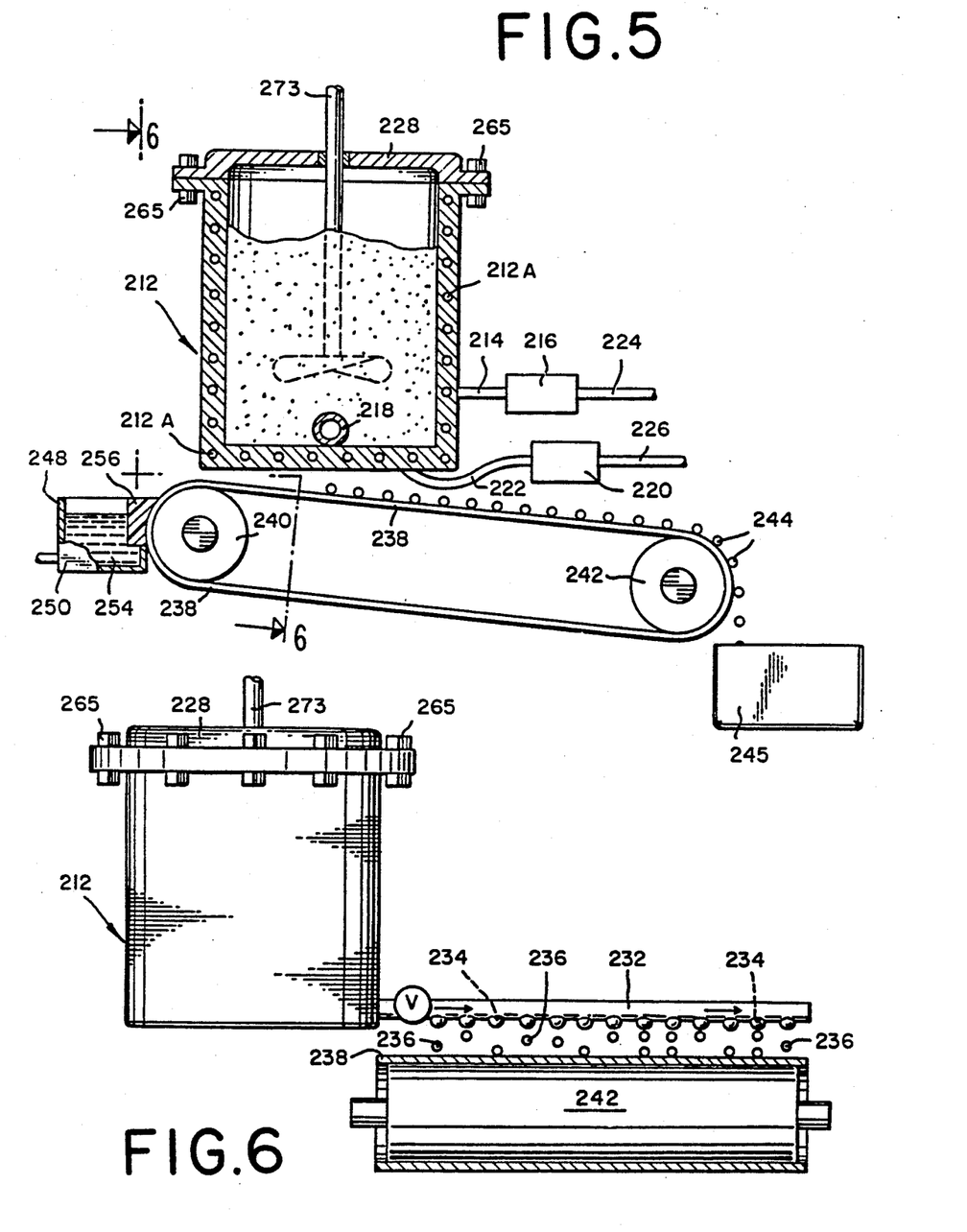
FIG. 5 is a partial side elevation and partial sectional view of an apparatus for forming polymer pellets scented with one of the epoxyoctahydrodimethylacetonaphthones or perfume compositions containing one of the epoxyoctahydrodimethylacetonaphthones of our invention.
FIG. 6 is a section taken along line 6—6 of FIG. 5.

FIG. 1 is the GLC profile of the reaction product of Example I (capillary GLC). The peak indicated by reference numeral 10 is the peak for the compound having the structure:

The peak indicated by reference numeral 12 is the peak for the compound having the structure:

FIG. 3 is the GLC profile for the reaction product of Example II. The peak indicated by reference numeral 30 is the peak for the compound having the structure:

Referring to FIGS. 5 and 6, the apparatus used in producing polymeric fragrances containing the epoxyoctahydrodimethylacetonaphthones of our invention comprises a device for forming scented polyolefin (for example) pellets which comprises a vat or container 212 into which a mixture of polyolefins such as polyethylene or an aromatic substance or scented material containing or consisting of at least one of the epoxyoctahydrodimethylacetonaphthones of our invention is placed. The container is closed by an air tight lid 228, and clamped to the container by bolts 265. A stirrer 273 traverses the lid or cover 228 in an air tight manner and is rotated in a suitable manner. A surrounding cylinder 212 having heating coils 212A which are supplied with electric current through cable 224 from a rheostat or control 216 is operated to maintain the temperature inside the container 212 such that polyethylene or other thermoplastic polymer in the container will be maintained in the molten or liquid state. It has been found advantageous to employ a colorless, odorless polymer (e.g., polyethylene) with a viscosity ranging between 180 and 220 saybolt seconds and having a melting point in the range of 220°-280° F. The heater 218 is operated to maintain the upper portion of the container 212 within a temperature range of from 250°-350° F. The bottom portion of the container is heated by means of heating coils 212A heated through a control 220 connected thereto through a connecting wire 226 with the control being connected to the heating coils with wire 222, to maintain the lower portion of the container within a temperature range of from 250°-350° F.

Thus, polymer (e.g., polyethylene) added to the container 212 is heated from 10-12 hours whereafter a scent or aroma imparting material which contains or consists of at least one of the epoxyoctahydrodimethylacetonaphthones of our invention is quickly added to the melt. The material must be compatible with the polyethylene and forms a homogeneous liquid melt therewith. The scented material containing or consisting of at least one of the epoxyoctahydrodimethylacetonaphthones of our invention is of a type for the particular aroma desired and formulated specifically for the scenting purpose for which the polyolefin will be employed. The heat resisting coils and aromatic materials in some instances are in solid or powdered form and may be employed and added to the polyolefin in the container 212. Generally about 10-30% by weight of scenting material is added to the polyolefin.

After scent imparting material containing or consisting of at least one of the epoxyoctahydrodimethylacetonaphthones of our invention is added to the container 212, the mixture is stirred for a few minutes, for example, 5-15 minutes and maintained within the temperature ranges indicated previously by the heating coils 212A and 218, respectively. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer (e.g., polyolefin) and aroma imparting material (containing or consisting of at least one of the epoxyoctahydrodimethylacetonaphthones of our invention) will continuously drop through the orifices 234 downwardly from the conduit 232. During this time, the temperature of the polymer (e.g., polyolefin) and aroma mixture containing or consisting of at least one of the epoxyoctahydrodimethylacetonaphthones of our invention in the container 212 is accurately controlled so that a temperature in the range of from about 210°-275° F. will exist in the conduit 232. The regulation of the temperature through the control 216 and the control 220 is essential in order to insure temperature balance to provide for the continuous dropping or dripping of molten polymer (e.g., polyolefin) and scenting material containing or consisting of at least one of the epoxyoctahydrodimethylacetonaphthones of our invention through the orifices 234 at a rate which will insure the formation of droplets 236 which will fall downwardly onto a moving conveyor belt 238 trained to run between conveyor wheels 240 and 242 beneath the conduit 232.

When the droplets 236 fall onto the conveyor 238, they form pellets 244 which harden almost instantaneously and fall off the end of the conveyor 238 into a container 259 which is advantageously filled with water or some other suitable cooling liquid in order to insure the rapid cooling of each of the pellets. The pellets 244 are then collected from the container 259 and utilized in a process, for example, to manufacture garbage bags which are fragranced.

A feature of this aspect of the process of our invention is in the provision for moistening the conveyor belt 238 to insure rapid formation of the solid polymer (e.g., polyolefin) scented pellets 244 without sticking to the belt. The belt 238 is advantageously of a material which will not normally stick to a melted plastic but the moistening means 248 insures a sufficiently cold temperature of the belt surface for the adequate formation of the pellets 244. The moistening means comprises a container 259 which is continuously fed with water 252 to maintain a level 254 for moistening a sponge element 256 which bears against the exterior surface of the belt 238.

THE INVENTION

The instant invention provides compounds, epoxyoctahydrodimethylacetonaphthones, defined according to the generic structure:

wherein $R_1$, $R_2$, $R_3$ and $R_4$ each represent hydrogen or methyl with the proviso that one of $R_3$ or $R_4$ is methyl and the other of $R_3$ or $R_4$ is hydrogen and $R_3$ and $R_4$ are not the same. The epoxyoctahydrodimethylacetonaphthones of our invention are useful in augmenting or enhancing the aroma of consumable materials, including perfume compositions, colognes and perfumed articles (including, but not limited to, solid or liquid anionic, cationic, nonionic or zwitterionic detergents, perfumed polymers, fabric softener compositions, fabric softener articles, cosmetic powders, hair preparations and the like).

Briefly, our invention contemplates imparting, augmenting or enhancing patchouli, musky, sweet, woody, animalic and civet aromas, with woody and patchouli topnotes to perfume compositions, perfumed articles and colognes.

The epoxyoctahydrodimethylacetonaphthones of our invention defined according to the generic structure:

also includes specific purified stereoisomers, for example, compounds defined according to the structures:

and wherein $R_1$ and $R_2$ are the same or different hydrogen or methyl.

The epoxyoctahydrodimethylacetonaphthones of our invention are prepared by carrying out a "epoxidation" reaction on compounds defined according to the generic structure:

using an epoxidizing agent such as peracetic acid or a compound defined according to the structure:

wherein R is hydrogen, acyl, benzoyl or substituted benzoyl according to the reaction:

The amount of compound defined according to the structure:

(e.g., peracetic acid)(35%)) may be from about 1 up to about 1.25 equivalents.

The reaction may be carried out at a temperature in the range of from about 30° C. up to about 50° C. with a preferred temperature of reaction being about 40° C.

The reaction may be carried out in the absence of a solvent or in the presence of an inert solvent such as a hydrocarbon, such as n-pentane or a chlorocarbon solvent such as methylene dichloride.

The epoxidizing agents are exemplified by the following:
mixture of hydrogen peroxide and formic acid;
m-chloroperbenzoic acid.

At the end of the reaction as stated, supra, the reaction product is extracted from the reaction mass or the reaction mass is washed, for example, with saturated sodium chloride. The reaction product is then distilled preferably by means of vacuum distillation using a fractionation column.

Examples of the products of our invention and their organoleptic properties as produced by means of the foregoing process are as follows:

TABLE I

| Structure of Epoxyoctahydrodimethylacetonaphthones | Perfumery Properties |
|---|---|
| Mixture of compounds having the structures:  and  prepared according to Example I, bulked distillation Fractions 2-5. | A patchouli, musky, sweet, woody, animalic and civet aroma with woody and patchouli topnotes. |
| Compound having the structure:  prepared according to Example II, bulked distillation Fractions 5-10. | A sweet, woody and patchouli aroma. |

The epoxyoctahydrodimethylacetonaphthones and one or more auxiliary ingredients, including for example, alcohols, aldehydes, ketones other than the epoxyoctahydrodimethylacetonaphthones of our invention, terpinic hydrocarbons, nitriles, esters, lactones, natural essential oils and synthetic essential oils, may be admixed so that the combined odors of the individual components produce a pleasant and desired fragrance, particularly and preferably in patchouli fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to their particular olfactory characteristics, however the overall sensory effect of the perfume composition will be at least the sum total of the effects of each of the ingredients. Thus, at least one of the epoxyoctahydrodimethylacetonaphthones of our invention can be used to alter, modify or enhance the aroma characteristics of a perfume composition, for example, by utilizing or moderating the olfactory reaction contributed by another ingredient in the composition.

The amount of one or more of the epoxyoctahydrodimethylacetonaphthones of our invention which will be effective in perfume compositions as well as in perfumed articles and colognes depends on many factors, including the other ingredients, their amounts and the effects which are desired. It has been found that perfume compositions containing as little as 0.01% of at least one of the epoxyoctahydrodimethylacetonaphthones of our invention or even less (e.g., 0.005%) can be used to impart, augment or enhance patchouli, musky, sweet, woody, animalic and civet aromas, with woody and patchouli topnotes to soaps, cosmetics, solid or liquid anionic, cationic, nonionic or zwitterionic detergents, fabric softener compositions, fabric softener articles, hair preparations and perfumed polymers. The amount employed can range up to 70% of the fragrance components and will depend on considerations of cost, nature of the end product, the effect desired on the finished product and the particular fragrance sought.

One or more of the epoxyoctahydrodimethylacetonaphthones of our invention are useful (taken alone or together with other ingredients in perfume compositions) as (an) olfactory component(s) in detergents and soaps, space odorants and deodorants, perfumes, colognes, toilet waters, bath preparations, such as creams, deodorants, hand lotions and sun screens; powders such as talcs, dusting powders, face powders and the like. When used as (an) olfactory component(s) as little as 1% of at least one of the epoxyoctahydrodimethylacetonaphthones of our invention or even less will suffice to impart intense and substantive patchouli, musky, sweet, woody, animalic and civet aromas, with woody and patchouli topnotes to patchouli formulations. Generally, no more than 20% of at least one of the epoxyoctahydrodimethylacetonaphthones of our invention based on the ultimate end product is required in the perfume composition.

Accordingly, in perfume compositions and colognes from about 0.01% up to about 70% of the perfume composition may be at least one of the epoxyoctahydrodimethylacetonaphthones of our invention. In perfumed articles, the quantity of at least one of the epoxyoctahydrodimethylacetonaphthones of our invention in the perfumed article may vary from about 0.005% up to about 25% of the perfumed article in the case of perfumed articles, for example, and up to about 8% in the case of solid or liquid anionic, cationic, nonionic or zwitterionic detergents, for example.

In addition, the perfume composition or fragrance composition of our invention can contain a vehicle, or carrier for at least one of the epoxyoctahydrodimethylacetonaphthones of our invention. The vehicle can be a liquid such as a non-toxic alcohol, such as ethyl alcohol or a non-toxic glycol, such as propylene glycol or the like. The carrier can also be an absorbent solid, such as a gum (e.g., gum arabic, xanthan gum, or guar gum or mixtures of same) or components for encapsulating the composition (such as gelatin as by means of coacervation or such as a ureaformaldehyde prepolymer when such a polymeric wall is formed around a liquid perfume composition center).

The following Examples I and II serve to illustrate the processes for preparing the epoxyoctahydrodimethylacetonaphthones of our invention. Examples following Example II (Examples III, et seq.) illustrate organoleptic utilites of the epoxyoctahydrodimethylacetonaphthones of our invention.

All parts and percentages given herein are by weight unless otherwise specified.

Example I

Preparation of METHYLOCTHAHYDRO-8,8-DIMETHYL-9,10-EPOXY NAPHTHALEN-2-YL KETONE Reaction:

Into a 1 liter reaction vessel equipped with stirrer, thermometer, reflux condenser and heating mantle is placed 260 grams of a 50:50 mixture of the compounds having the structures:

and and 25 grams of sodium carbonate. The reaction mass is heated to 45°-50° C. and maintained at 45°-50° C. with stirring.

Over a period of one hour, 230 grams of peracetic acid is added to the reaction mass while maintaining the temperature at 45°-50° C.

The reaction mass is then washed with one volume of water, followed by one volume of 50% sodium hydroxide (aqueous).

The reaction mass is then distilled on a fractionation column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 23/25 | 23/110 | 50/3 | 100% |
| 2 | 132 | 152 | 3 | 9:1 |
| 3 | 128 | 160 | 3 | 9:1 |
| 4 | 128 | 162 | 3 | 1:9 |
| 5 | 128 | 165 | 3 | 1:9 |
| 6 | 128 | 166 | 2 | 1:9. |

Fractions 2-5 are bulked. Bulked distillation Fractions 2-5 have a patchouli, musky, sweet, woody, animalic and civet aroma, with woody and patchouli topnotes.

FIG. 1 is the GLC profile for the reaction product.

Figure 2:
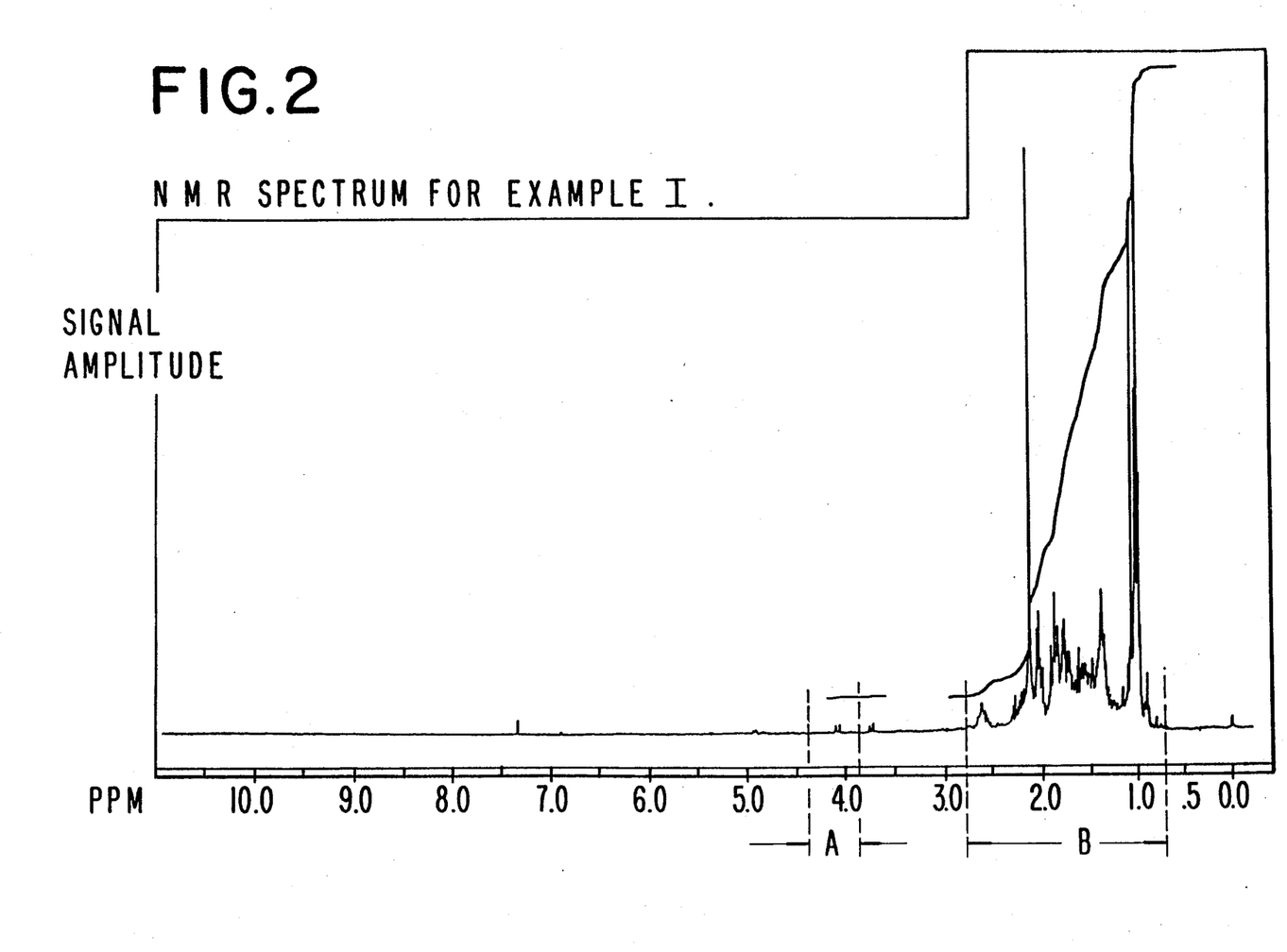
FIG. 2 is the NMR spectrum for the mixture of compounds having the structures.

FIG. 2 is the NMR spectrum for the reaction product which has the two compounds having the structures:

and

Reaction:

Into a 3 liter reaction vessel equipped with stirrer, thermometer, reflux condenser and heating mantle are placed 1,404 grams of the compound having the structure:

and 106 grams of sodium carbonate. With stirring, the reaction mass is heated to 45° C.

Over a three hour period while maintaining the reaction mass at 40°-50° C., 1,308 grams of peracetic acid is added to the reaction mass. Since the reaction is exothermic, a cooling bath is used to replace the heating mantle in order to maintain the temperature at 40°-50° C.

After the peracetic acid is added, the reaction mass is stirred for a period of one hour at 45° C.

The reaction mass is then washed with two liter portions of 25% aqueous sodium hydroxide.

The reaction mass is then distilled on a fractionation column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 25/30 | 25/16 | 50/5 | 100% |
| 2 | 135 | 108 | 3 | 9:1 |
| 3 | 138 | 168 | 3 | 9:1 |
| 4 | 138 | 170 | 3 | 1:9 |
| 5 | 133 | 170 | 2 | 1:9 |
| 6 | 132 | 172 | 2 | 1:9 |
| 7 | 130 | 172 | 2 | 1:9 |
| 8 | 130 | 174 | 1 | 1:9 |
| 9 | 130 | 178 | 1 | 1:9 |
| 10 | 130 | 180 | 1 | 1:9 |
| 11 | 130 | 182 | 1 | 1:9 |
| 12 | 130 | 188 | 1 | 1:9 |
| 13 | 130 | 198 | 1 | 1:9. |

Fractions 5-10 are bulked. Bulked distillation Fractions 5-10 have a sweet, woody and patchouli aroma.

Figure 4:
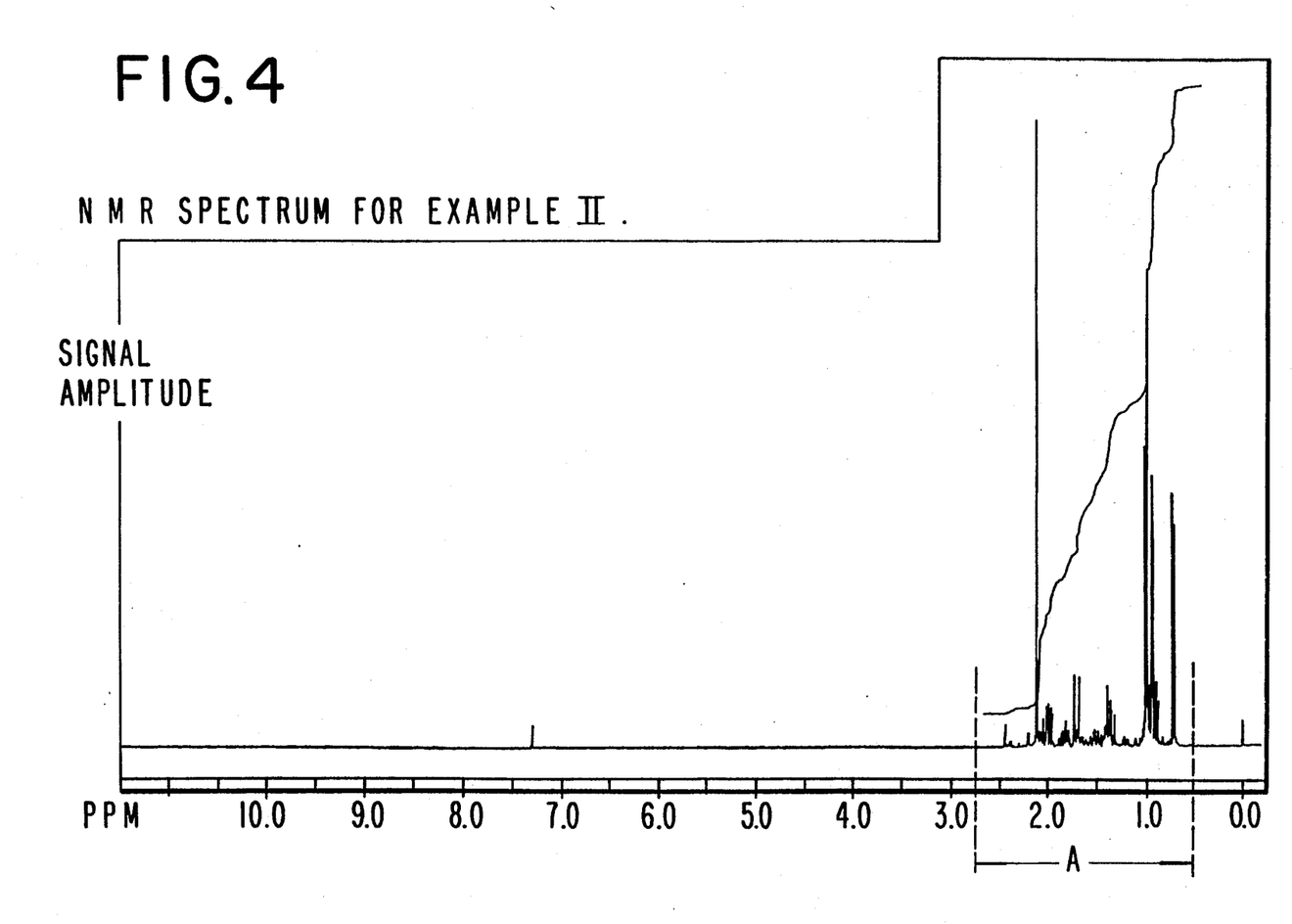
FIG. 4 is the NMR spectrum for the compound having the structure.

FIG. 3 is the GLC profile for the reaction product. The peak indicated by reference numeral 30 is the peak for the reaction product which is the compound having the structure:

FIG. 4 is the NMR spectrum for the compound having the structure:

EXAMPLE III

Perfume Compositions

The epoxyoctahydrodimethylacetonaphthones of our invention produced according to Examples I and II have very long-lasting patchouli, musky, sweet, woody, animalic and civet aromas, with woody and patchouli topnotes. These aroma nuances may be utilized to a great extent in inexpensive functional products. The following pine fragrance demonstrates the use of these materials in perfume compositions.

| Ingredients | Parts by Weight EXAMPLE III(A) | EXAMPLE III(B) |
|---|---|---|
| Isobornyl acetate | 100 | 100 |
| Camphor | 10 | 10 |
| Terpineol | 25 | 25 |
| Fir Balsam Absolute (50% in Diethyl Phthalate) | 20 | 20 |
| Coumarin | 4 | 4 |
| Linalool | 30 | 30 |
| Anethol | 2 | 2 |
| Fenchyl Alcohol | 10 | 10 |
| Lemon Terpenes Washed | 50 | 50 |
| Borneol | 5 | 5 |
| Galbanum Oil | 5 | 5 |
| Turpentine Russian | 150 | 150 |
| Pinus Pumilionus | 50 | 50 |
| Eucalyptol | 50 | 50 |
| 2,2,6-Trimethyl-1-cyclohexene-1-carboxaldehyde | 5 | 5 |
| Maltol (1% in Diethyl Phthalate) | 5 | 5 |
| Mixture of compounds having the structures: prepared according to Example I, bulked distillation Fractions 2-5. | 12 | 0 |
| Compound having the structure: prepared according to Example II, bulked distillation Fractions 5-10. | 0 | 12 |

The mixture of compounds having the structure:

prepared according to Example I imparts to this pine fragrance patchouli, musky, sweet, woody, animalic and civet undertones, with woody and patchouli topnotes. Accordingly, the perfume composition of Example III(A) can be described as "piney, with patchouli, musky, sweet, woody, animalic and civet undertones and woody and patchouli topnotes".

The compound having the structure:

prepared according to Example II adds to this pine formulation sweet, woody and patchouli undertones. Accordingly, the perfume formulation of Example III(B) can be described as "piney, with sweet, woody and patchouli undertones".

EXAMPLE IV

A Cosmetic Powder Preparation

A cosmetic powder is prepared by mixing in a ball mill 100 grams of talcum powder with 0.25 grams of one of the substances set forth in Table II below containing at least one of the epoxyoctahydrodimethylacetonaphthones of our invention. Each of the cosmetic powders has an excellent substantive aroma as described in Table II below.

TABLE II

| Perfumery Substance | Aroma Nuance |
|---|---|
| Mixture of compounds having the structures: [structure] and [structure] prepared according to Example I, bulked distillation Fractions 2-5. | A patchouli, musky, sweet, woody, animalic and civet aroma with woody and patchouli topnotes. |
| The compound having the structure: [structure] prepared according to Example II, bulked distillation Fractions 5-10. | A sweet, woody and patchouli aroma profile. |
| Perfume composition of Example III(A). | Piney, with patchouli, musky, sweet, woody, animalic and civet undertones and woody and patchouli topnotes. |
| Perfume composition of Example III(B). | Piney, with sweet, woody and patchouli undertones. |

EXAMPLE V

Perfumed Liquid Detergent

Concentrated liquid detergents (Lysine salt of n-dodecylbenzene sulfonic acid as more specifically described in U.S. Pat. No. 3,948,818 issued on Apr. 6, 1976 the specification for which is incorporated herein) with aromas as set forth in Table II of Example IV, supra, are prepared containing 0.10%, 0.15%, 0.20%, 0.25%, 0.30% and 0.35% of each of the substances of Table II of Example IV. They are prepared by adding and homogeneously admixing the appropriate quantity of one of the substances of Table II of Example IV in the liquid detergent. The detergents all possess excellent aromas as set forth in Table II of Example IV.

EXAMPLE VI

Preparation of a Cologne and Handkerchief Perfume

The substances set forth in Table II of Example IV are incorporated separately into colognes at concentrations of 2.0%, 2.5%, 3.0%, 3.5%, 4.0%, 4.5% and 5.0% in 75%, 80%, 85% and 90% aqueous food grade ethanol solutions; and into handkerchief perfumes at concentrations of 15%, 20%, 25% and 30%, in 80%, 85%, 90% and 95% aqueous food grade ethanol solutions. Distinctive aromas as set forth in Table II of Example IV, supra, are imparted to the colognes and to the handkerchief perfume compositions at all levels indicated.

EXAMPLE VII

Preparation of a Soap Composition

One hundred grams of soap chips (IVORY ®, produced by Procter & Gamble Company of Cincinnati, Ohio) are admixed with 1 gram of each of the substances of Table II of Example IV, supra, until homogeneous compositions are obtained. The homogeneous compositions are each separated then heated under 3 atmospheres pressure at 180° C. for a period of 3 hours and the resulting liquid samples are placed in soap molds. The resulting soap cake, on cooling, manifest excellent long-lasting aromas as set forth in Table II of Example IV, supra.

EXAMPLE VIII

Preparation of Solid Detergent Compositions

Detergents are prepared from the following ingredients according to Example I of Canadian Patent No. 1,007,948 the specification for which is incorporated by reference herein:

| Ingredients | Parts by Weight |
|---|---|
| NEODOL ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. A total of 100 grams of said detergent is admixed separately with 0.10, 0.15, 0.20 and 0.25 grams of each of the substances of Table II of Example IV. Each of the detergent samples has an excellent aroma as set forth in Table II of Example IV.

EXAMPLE IX

Drier-Added Fabric Softener Articles

Utilizing the procedure of Example I at column 15 of U.S. Pat. No. 3,632,396, the specification for which is incorporated by reference herein, a non-woven cloth substrate useful as a drier-added fabric softening article of manufacture is prepared wherein the substrate, the substrate coating and the outer coating and the perfuming material are as follows:
1. A water "dissolvable" paper ("Dissolvo Paper")
2. Adogen 448 (m.p. about 140° F.) as the substrate coating; and
3. An outer coating having the following formulation (m.p. about 150° F.):

57% - C$_{20\text{-}22}$ HAPS
22% - isopropyl alcohol
20% - antistatic agent
1% - of one of the substances of Table II of Example IV, supra.

Fabric softening compositions containing one of the substances of Table II of Example IV consist essentially of a substrate having a weight of about 3 grams per 100 square inches of substrate coating having a weight of about 1.85 grams per 100 square inches; and an outer coating having a weight of about 1.4 grams per 100 square inches thereby providing a total aromatized substrate and outer coating weight ratio of about 1:1 by weight of the substrate.

Pleasant aromas as set forth in Table II of Example IV are imparted to the head space in the dryer on operation thereof using the said drier-added fabric softening non-woven fabric.

What is claimed is:

1. At least one epoxyoctahydrodimethylacetonaphthone defined according to the structure:

wherein R$_1$, R$_2$, R$_3$ and R$_4$ are hydrogen or methyl with the proviso that when R$_3$ is methyl, R$_4$ is hydrogen and when R$_4$ is methyl R$_3$ is hydrogen.

2. The epoxyoctahydrodimethylacetonaphthone of claim 1 having the structure:

3. The epoxyoctahydrodimethylacetonaphthone of claim 1 having the structure:

4. The epoxyoctahydrodimethylacetonaphthone of claim 1 having the structure:

5. A mixture of epoxyoctahydrodimethylacetonaphthones having the structures:

and

6. A process for augmenting or enhancing the aroma of a perfume composition, cologne or perfumed article comprising the step of adding to said perfume composition, perfumed article or cologne, an aroma augmenting or enhancing quantity of at least one epoxyoctahydrodimethylacetonaphthone defined according to claim 1.

7. A process for augmenting or enhancing the aroma of a perfume composition, cologne or perfumed article comprising the step of adding to said perfume composition, perfumed article or cologne, an aroma augmenting or enhancing quantity of at least one epoxyoctahydrodimethylacetonaphthone defined according to claim 2.

8. A process for augmenting or enhancing the aroma of a perfume composition, cologne or perfumed article comprising the step of adding to said perfume composition, perfumed article or cologne, an aroma augmenting or enhancing quantity of at least one epoxyoctahydrodimethylacetonaphthone defined according to claim 3.

9. A process for augmenting or enhancing the aroma of a perfume composition, cologne or perfumed article comprising the step of adding to said perfume composition, perfumed article or cologne, an aroma augmenting or enhancing quantity of at least one epoxyoctahydrodimethylacetonaphthone defined according to claim 4.

10. A process for augmenting or enhancing the aroma of a perfume composition, cologne or perfumed article comprising the step of adding to said perfume composition, perfumed article or cologne, an aroma augmenting or enhancing quantity of at least one epoxyoctahydrodimethylacetonaphthone defined according to claim 5.

11. A perfume composition comprising a perfume base and intimately admixed therewith, an aroma imparting, augmenting or enhancing quantity of at least one of the epoxyoctahydrodimethylacetonaphthone defined according to claim 1.

12. A perfume composition comprising a perfume base and intimately admixed therewith, an aroma imparting, augmenting or enhancing quantity of at least one of the epoxyoctahydrodimethylacetonaphthone defined according to claim 2.

13. A perfume composition comprising a perfume base and intimately admixed therewith, an aroma imparting, augmenting or enhancing quantity of at least one of the epoxyoctahydrodimethylacetonaphthones defined according to claim 3.

14. A perfume composition comprising a perfume base and intimately admixed therewith, an aroma imparting, augmenting or enhancing quantity of at least one of the epoxyoctahydrodimethylacetonaphthones defined according to claim 4.

15. A perfume composition comprising a perfume base and intimately admixed therewith, an aroma imparting, augmenting or enhancing quantity of at least one of the epoxyoctahydrodimethylacetonaphthones defined according to claim 5.

16. A perfume polymer comprising a porous polymer having imbedded therein, an aroma imparting, augmenting or enhancing amount of at least one epoxyoctahydrodimethylacetonaphthone defined according to claim 1.

17. A perfume polymer comprising a porous polymer having imbedded therein, an aroma imparting, augmenting or enhancing amount of at least one epoxyoctahydrodimethylacetonaphthone defined according to claim 2.

18. A perfume polymer comprising a porous polymer having imbedded therein, an aroma imparting, augmenting or enhancing amount of at least one epoxyoctahydrodimethylacetonaphthone defined according to claim 3.

19. A perfume polymer comprising a porous polymer having imbedded therein, an aroma imparting, augmenting or enhancing amount of at least one epoxyoctahydrodimethylacetonaphthone defined according to claim 4.

20. A perfume polymer comprising a porous polymer having imbedded therein, an aroma imparting, augmenting or enhancing amount of at least one epoxyoctahydrodimethylacetonaphthone defined according to claim 5.

* * * * *